United States Patent
Stoer et al.

(10) Patent No.: US 10,517,809 B2
(45) Date of Patent: *Dec. 31, 2019

(54) COMBINATION OF ISOSORBIDE DIESTERS WITH NON-IONIC SURFACTANTS FOR USE AS PEARLIZING AGENT

(71) Applicant: BASF SE, Ludwigshafen am Rhein (DE)

(72) Inventors: Claudia Stoer, Duesseldorf (DE); Markus Weissenegger, Duesseldorf (DE); Claus Nieendick, Krefeld (DE); Mirella Winzek, Titz (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,669

(22) PCT Filed: May 17, 2016

(86) PCT No.: PCT/EP2016/060959
§ 371 (c)(1),
(2) Date: Nov. 20, 2017

(87) PCT Pub. No.: WO2016/188789
PCT Pub. Date: Dec. 1, 2016

(65) Prior Publication Data
US 2018/0280273 A1 Oct. 4, 2018

(30) Foreign Application Priority Data

May 27, 2015 (EP) .................................... 15169332

(51) Int. Cl.
| | | |
|---|---|---|
| *A61K 8/60* | (2006.01) | |
| *A61Q 19/00* | (2006.01) | |
| *A61K 8/37* | (2006.01) | |
| *A61Q 5/02* | (2006.01) | |

(52) U.S. Cl.
CPC .............. *A61K 8/604* (2013.01); *A61K 8/37* (2013.01); *A61K 8/60* (2013.01); *A61Q 5/02* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,403,508 A | 4/1995 | Reng et al. | |
| 2005/0172859 A1 | 8/2005 | Nieendick et al. | |
| 2011/0091393 A1* | 4/2011 | Simmonds | A61K 8/604 424/49 |
| 2013/0011347 A1* | 1/2013 | Tanner | A61K 8/347 424/59 |
| 2014/0323592 A1 | 10/2014 | Pilz et al. | |

FOREIGN PATENT DOCUMENTS

| | | |
|---|---|---|
| EP | 0 581 193 A2 | 2/1994 |
| EP | 2 239 315 A1 | 10/2010 |
| WO | WO-03/052037 A1 | 6/2003 |
| WO | WO-2013/041388 A1 | 3/2013 |

OTHER PUBLICATIONS

International Search Report for PCT Patent Application No. PCT/EP2016/060959, dated Aug. 2, 2016.

* cited by examiner

*Primary Examiner* — Nicole P Babson
(74) *Attorney, Agent, or Firm* — Marshall, Gerstein & Borun LLP

(57) ABSTRACT

A description is given of a composition comprising at least one isosorbide diester as constituent I and at least one non-ionic surfactant as constituent II and also of a method for the preparation thereof. In addition, the present invention relates to the use of this composition as pearlizing agent in cosmetic compositions.

16 Claims, No Drawings

COMBINATION OF ISOSORBIDE DIESTERS WITH NON-IONIC SURFACTANTS FOR USE AS PEARLIZING AGENT

CROSS-REFRENCE TO RELATED APPLICATIONS

This application is the U.S. National Phase of PCT/EP2016/060959, filed May 17, 2016, which claims the benefit of European Patent Application No. 15169332.2, filed May 27, 2015.

The present invention relates to compositions comprising at least one isosorbide diester of a saturated fatty acid and at least one non-ionic surfactant and also to methods for the preparation thereof. The present invention further relates to the use of the corresponding compositions as pearlizing agents in cosmetic compositions.

Pearlizing agents are frequently used in cosmetic compositions to improve the aesthetics of the corresponding preparations and to give them an especially caring appearance. In order to meet the high market demands with regard to sensory properties, new pearlizing agents are accordingly continually being developed and the suitability thereof in cosmetic compositions tested.

The pearlizing agents commercially available or described at present are still not satisfactory for use in cosmetic compositions and there accordingly furthermore exists a requirement for the provision of new ingredients which are suitable for use in cosmetic compositions as pearlizing agents.

A multitude of formulations is known in the prior art which impart the desired pearlescence to surface-active cleaning compositions. For instance, according to EP-B1 0 569 843 for example, non-ionic free-flowing pearlizing dispersions can be obtained by preparing mixtures of 5 to 30% by weight acylated polyglycols and 0.1 to 20% by weight selected non-ionic surfactants. Free-flowing, preservative-free pearlizing dispersions are also known from EP-A2 0 581 193, which comprise acylated polyglycol ethers, betaines, anionic surfactants and glycerol.

Known from the American patent application US 2014/0323592 is the use of isosorbide dicaprylate as thickener in cosmetic compositions such as shampoos.

Despite the variety of compositions, there exists in the market a continuous demand for novel pearlizing waxes, in particular for pearlizing waxes which as far as possible do not comprise any ethylene oxide and/or propylene oxide units, since these can be used widely with surfactants without ethylene oxide units both in classical and in so-called "green" cleaning compositions. Nevertheless, it is expected from the novel pearlizing waxes that they have a comparable performance spectrum with respect to pearlescence, particularly whiteness and brilliance, such as the widespread polyethylene glycol stearates. In addition, the pearlizing waxes should also be sufficiently compatible with other sensitive or critical ingredients, such as silicones, so that the stability of the cleaning compositions is not impaired. Furthermore, it is expected that the pearlizing agents can be readily incorporated into the cosmetic formulation, i.e. without great technical complexity and energy expenditure. This should be carried out as simply as possible by stirring at room temperature without time- and cost-intensive heating of the cosmetic formulation. In addition, many manufacturers of cosmetic compositions have a requirement for pearlizing waxes which can be formulated as a concentrate in order to avoid unnecessary transport and storage costs. These concentrates should also be free-flowing in order to ensure easy preparation of the cosmetic formulation.

In the context of sustainability, compounds that are ecologically sustainable and sufficiently biodegradable are also desirable.

Specific compositions comprising isosorbide derivatives have now been developed according to the invention which can advantageously be used in cosmetic compositions or detergents in combination with non-ionic surfactants.

Accordingly, the present invention relates to a composition comprising at least one pearlizing wax as first constituent, comprising at least one isosorbide diester of a saturated $C_{12}$-$C_{24}$ fatty acid, and at least one second constituent, comprising a non-ionic surfactant.

It has been found in accordance with the invention that a composition comprising a pearlizing wax with at least one isosorbide diester of a saturated $C_{12}$-$C_{24}$ fatty acid and at least one non-ionic surfactant, results in an improved pearlizing effect in cosmetic compositions.

The present invention is now described in detail.

Pearlizing Wax (First Constituent of the Composition According to the Invention)

The composition according to the invention comprises a pearlizing wax as first constituent. In the context of the invention, the term "pearlizing wax" is used for wax-like compounds or mixtures of compounds which produce a pearlescent effect (instead of the term "pearlizing", the terms "nacre" or "luster" are used). In the context of the invention, the pearlescent effect is assessed visually as whiteness and brilliance, the intensity of the shimmer, compared to the standard ethylene glycol distearate (EGDS) as pearlizing wax.

Isosorbide Diester as Constituent of the Pearlizing Wax

The pearlizing wax as first constituent of the composition according to the invention comprises at least one isosorbide diester of a saturated $C_{12}$-$C_{24}$ fatty acid. Isosorbide (or 1,4:3,6-dianhydrosorbitol) is the anhydride of sorbitol and is commercially available. It can, for example, be obtained by heating sorbitol in the presence of concentrated sulfuric or hydrochloric acid. In addition, isosorbide can be obtained starting from suitable polysaccharides after hydrolysis to give D-glucose and subsequent reduction to give D-sorbitol through intramolecular double dehydration. On an industrial scale, starch or cellulose is used as source of raw material. Isosorbide is an attractive building block for applications in the cosmetic field and in the detergent field since it is prepared from renewable raw materials.

Different isosorbide mono- and/or diesters can be obtained by processes known per se to a person skilled in the art.

The isosorbide diester to be used according to the invention in the pearlizing wax has the general formula (I)

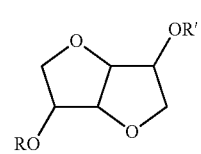

where R and R' are each independently a COR" radical in which R" is a linear saturated alkyl radical having 11 to 23 carbon atoms. The isosorbide diester to be used according to the invention can be a homogeneous or mixed diester.

The general formula (I) represented above also comprises, in the context of the present invention, all stereoisomers of the isosorbide, in particular isoidide and isomannide, and also any mixtures thereof. Furthermore, the general formula (I) also comprises all combinations of the R and R' radicals with each other. In the context of the present invention therefore, the term "an isosorbide diester of a saturated fatty acid" is also understood to mean a diester of the isosorbide which has been esterified with two different saturated fatty acids.

The pearlizing wax comprises an isosorbide diester of a saturated $C_{12}$ to $C_{24}$-fatty acid of the general formula (I), which has already been described above.

The saturated $C_{12}$ to $C_{24}$-fatty acids are suitable as fatty acids for the formation of the isosorbide diester. These are preferably selected from the group consisting of lauric acid, tridecanoic acid, myristic acid, pentadecanoic acid, palmitic acid, heptadecanoic acid, stearic acid, nonadecanoic acid, arachidic acid, heneicosanoic acid, behenic acid and lignoceric acid.

In a preferred embodiment, the isosorbide diester is a diester of isosorbide with a saturated $C_{12}$ to $C_{22}$-fatty acid, more preferably a diester of isosorbide with a saturated $C_{12}$ to $C_{20}$-fatty acid and more preferably still a diester of isosorbide with a saturated $C_{16}$ to $C_{18}$-fatty acid.

In the context of the present invention, the diesters of isosorbide with a $C_{16}$ to $C_{18}$-fatty acid have in particular proven to be suitable for achieving the desired pearlizing properties in cosmetic compositions.

Accordingly, in an additional even more preferred embodiment of the composition according to the invention, the pearlizing wax comprises an isosorbide diester selected from the group consisting of isosorbide distearate, isosorbide dipalmitate, isosorbide palmitate stearate and mixtures of the abovementioned compounds.

Furthermore, the pearlizing wax of the composition according to the invention comprises in particular a mixture of diesters of the isosorbide, a mixture of isosorbide diesters comprising isosorbide distearate being particularly preferred.

In a very particularly preferred embodiment of the composition according to the invention, the pearlizing wax comprises a mixture of isosorbide distearate, isosorbide dipalmitate and isosorbide palmitate stearate.

If, in the context of the present invention, this particularly preferred mixture of isosorbide distearate, isosorbide dipalmitate and isosorbide palmitate stearate is used as pearlizing wax, the ratio by weight of isosorbide dipalmitate to isosorbide distearate is preferably from 45:55 to 1:99, more preferably from 40:60 to 1:99, more preferably still from 30:70 to 1:99, more preferably still from 30:70 to 2:98. When use is made of a mixture of isosorbide distearate and isosorbide dipalmitate with the relative ratios mentioned above, i.e. in particular with an excess of isosorbide distearate, the pearlizing properties are very particularly pronounced.

The isosorbide diester can be present in the composition according to the invention in an amount of at least 70% by weight, more preferably at least 75% by weight, even more preferably at least 80% by weight, even more preferably at least 82% by weight, based in each case on the pearlizing wax as first constituent of the composition according to the invention.

The isosorbide diester can be present in the composition according to the invention in an amount of at most 95% by weight, more preferably at most 90% by weight, even more preferably at most 88% by weight, based in each case on the pearlizing wax as first constituent of the composition according to the invention.

The isosorbide diester is preferably present in the composition according to the invention in an amount of 75% by weight to 95% by weight, more preferably 80% by weight to 90% by weight and more preferably still 82% by weight to 88% by weight, based in each case on the pearlizing wax as first constituent of the composition according to the invention, in order to obtain a good pearlizing effect.

Isosorbide Monoester as Constituent of the Pearlizing Wax

In the pearlizing wax to be used according to the invention, an isosorbide monoester may also be present. It preferably concerns here a monoester of isosorbide with a saturated $C_{12}$ to $C_{24}$-fatty acid of the general formula (II):

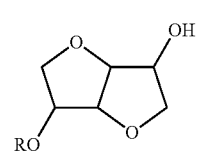

(II)

where R is a COR' radical in which R' is a linear saturated alkyl radical having 11 to 23 carbon atoms.

The same fatty acids, which are also used above for the isosorbide diester, are suitable for the preparation of the isosorbide monoester. In this respect, reference is made to the above embodiments.

If an isosorbide monoester is present in the pearlizing wax, it is preferably an isosorbide monoester with a $C_{16}$ to $C_{18}$-fatty acid.

In particular, it can be an isosorbide monoester which is selected from the group consisting of isosorbide monostearate, isosorbide monopalmitate and mixtures of the abovementioned compounds.

Furthermore, the pearlizing wax of the composition according to the invention may comprise in particular a mixture of monoesters of the isosorbide, a mixture of isosorbide monoesters comprising isosorbide monostearate being particularly preferred.

In a very particularly preferred embodiment, the isosorbide monoester of the pearlizing wax is a mixture of isosorbide monostearate and isosorbide monopalmitate.

If, in the context of the present invention, this mixture of isosorbide monostearate and isosorbide monopalmitate is used in the pearlizing wax, the ratio by weight of isosorbide monopalmitate to isosorbide monostearate is preferably from 45:55 to 1:99, more preferably from 40:60 to 1:99, more preferably still from 30:70 to 1:99, more preferably still from 30:70 to 2:98. When use is made of a mixture of isosorbide monostearate and isosorbide monopalmitate in the relative proportions mentioned above, the pearlizing properties are very particularly pronounced.

The isosorbide monoester can be present in the composition according to the invention in an amount of at least 0.01% by weight, more preferably at least 0.5% by weight, even more preferably at least 1% by weight, based in each case on the pearlizing wax as first constituent of the composition according to the invention.

The isosorbide monoester can be present in the composition according to the invention in an amount of at most 20% by weight, more preferably at most 15% by weight, even more preferably at most 10% by weight, based in each case on the pearlizing wax as first constituent of the composition according to the invention.

The isosorbide monoester is preferably present in the composition according to the invention in an amount of 0.01% by weight to 20% by weight, more preferably 0.5% by weight to 15% by weight and more preferably still 1% by weight to 10% by weight, based in each case on the pearlizing wax as first constituent of the composition according to the invention, in order to obtain a good pearlizing effect.

Fatty Acid as Constituent of the Pearlizing Wax

A fatty acid may also be present in the pearlizing wax of the composition according to the invention. It preferably concerns here a fatty acid which has already been used above for the preparation of the isosorbide diester or isosorbide monoester. In this respect, reference is made to the above embodiments.

If the pearlizing wax comprises a fatty acid, it is preferably a $C_{16}$ to $C_{18}$-fatty acid which is particularly preferably selected from the group consisting of stearic acid, palmitic acid and mixtures thereof.

In a very particularly preferred embodiment, the fatty acid is a mixture of stearic acid and palmitic acid.

If, in the context of the present invention, a mixture of stearic acid and palmitic acid is used in the pearlizing wax, the ratio by weight of palmitic acid to stearic acid is preferably from 45:55 to 1:99, more preferably from 40:60 to 1:99, more preferably still from 30:70 to 1:99, more preferably still from 30:70 to 2:98.

The fatty acid can be present in the composition according to the invention in an amount of at most 20% by weight, more preferably at most 17% by weight, even more preferably at most 14% by weight, based in each case on the pearlizing wax as first constituent of the composition according to the invention.

The fatty acid can be present in the composition according to the invention in an amount of at least 1% by weight, more preferably at least 3% by weight, even more preferably at least 5% by weight, based in each case on the pearlizing wax as first constituent of the composition according to the invention.

The fatty acid is preferably present in the wax composition of the pearlescent concentrate according to the invention in an amount of 1% by weight to 20% by weight, more preferably 3% by weight to 17% by weight and more preferably still 5% by weight to 14% by weight, based in each case on the pearlizing wax as first constituent of the composition according to the invention.

Non-ionic Surfactant (Second Constituent of the Composition According to the Invention)

In the composition according to the invention, a non-ionic surfactant is used as second constituent.

In the context of the present invention, the term a "non-ionic surfactant" is also understood to mean a mixture of two or more non-ionic surfactants.

The non-ionic surfactant is, for example, a fatty alcohol polyglycol ether; alkylphenol polyglycol ether; fatty acid polyglycol ester; fatty acid amide polyglycol ether; fatty amine polyglycol ether; polyol fatty ester, in particular fatty acid glycerol ester, specifically fatty acid glycerol monoester, fatty acid glycerol diester and fatty acid glycerol triester, wherein the content of fatty acid monoester in such a mixture is more than 40% by weight; alkoxylated triglycerides; mixed ethers or mixed formals; optionally partially oxidized alk(en)yl polyglycosides or glucuronic acid derivatives; fatty acid N-alkylglucamides; protein hydrolysates (in particular wheat-based plant products); polyol fatty acid esters; sugar esters; sorbitan esters; polysorbates and amine oxides.

If the non-ionic surfactants contain polyglycol ether chains, these may have a conventional homolog distribution, but preferably have a narrow homolog distribution.

The non-ionic surfactant is preferably a non-ionic surfactant free of ethylene oxide units.

Moreover, preference is given to fatty acid glycerol esters, specifically fatty acid glycerol monoesters, fatty acid glycerol diesters and fatty acid glycerol triesters, wherein the monoester content in the mixture of mono, di- and triesters is more than 40% by weight, and alkyl polyglycosides.

In a very particularly preferred embodiment, the non-ionic surfactant is an alkyl polyglycoside.

Alkyl polyglycosides are known non-ionic surfactants which have the formula (III),

$$R^1O\text{-}[G]_p \qquad (III)$$

in which $R^1$ is an alkyl radical having 4 to 22 carbon atoms,

G is a sugar radical having five or six carbon atoms, and p is a number from 1 to 10.

They can be obtained by the relevant methods of preparative organic chemistry. As a representative of the extensive literature on this subject, reference can be made to the review by Biermann et al. in Starch/Stärke 45, 281 (1993), B. Salka in Cosm. Toil. 108, 89 (1993) and also to J. Kahre et al. in SÖFW-Journal book 8, 598 (1995).

The alkyl polyglycosides can be derived from aldoses or ketoses having 5 or 6 carbon atoms, preferably from glucose. The preferred alkyl polyglycosides are therefore alkyl polyoglucosides. The index number p in the general formula (I) specifies the degree of polymerization (DP), i.e. the distribution of mono- and polyoglycosides, and is a number between 1 and 10. Whereas p in a given compound must always be an integer and can here in particular assume the values p=1 to 6, the value p for a particular alkyl polyglycoside is an analytically determined calculated parameter which in most cases is a fraction. Preferably, alkyl polyglycosides are used with an average degree of polymerization p of 1.1 to 3.0. Preference is given to those alkyl polyglycosides, from a technical applications point of view, for which the degree of polymerization is less than 1.7 and is particularly between 1.2 and 1.7.

The alkyl radical $R^1$ can be derived from primary alcohols having 4 to 22, preferably 6 to 18 carbon atoms.

In one embodiment of the present invention, the alkyl radical $R^1$ is derived from lower primary alcohols preferably having 4 to 11, more preferably 8 or 10 carbon atoms.

Typical examples are butanol, caproic alcohol, caprylic alcohol, capric alcohol and undecyl alcohol, and also their technical grade mixtures, as obtained, for example, in the hydrogenation of technical grade fatty acid methyl esters or during the hydrogenation of aldehydes from Roelen's oxo synthesis. Preference is given to alkyl polyglucosides having a chain length of $C_8$-$C_{10}$ (DP=1 to 3), which are obtained as forerun in the distillative separation of technical grade $C_8$-$C_{18}$-coconut fatty alcohol, and may be contaminated with a fraction of less than 6% by weight $C_{12}$-alcohol and also alkyl polyglucosides based on technical grade $C_{9/11}$-oxo alcohols (DP=1 to 3).

The alkyl radical $R^1$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and also technical grade mixtures thereof which may be obtained as described above. Preference is given to alkyl polyglucosides based on hardened $C_{12/14}$-coconut fatty alcohol with a DP of 1 to 3.

In the context of the present invention, very particular preference is given to compositions comprising a mixture of different alkyl polyglycosides of the formula (III), in which $R^1$ of one alkyl polyglycoside is derived from a lower primary alcohol having 4 to 11 carbon atoms, preferably 8 and/or 10 carbon atoms, and in which $R^1$ of the other alkyl polyglycoside is derived from a primary higher alcohol having 12 to 22 carbon atoms, preferably 12 to 16 carbon atoms.

In the context of the present invention, preference is given in particular to mixtures of different alkyl polyglycosides of the formula (III) as constituent II, in which $R^1$ is derived from primary alcohol mixtures comprising 10 to 50% by weight 8 and 10 carbon atoms and 50 to 90% by weight 12 to 16 carbon atoms, in which low amounts, in particular less than 10% by weight based on the alcohol mixture, can be derived from alcohols having fewer or more carbon atoms.

Such mixtures of different alkyl polyglycosides may be obtained by mixing the alkyl polyglycosides or by using such alcohol mixtures in the preparation of the alkyl polyglycosides.

Preferred Embodiments of the Composition According to the Invention

Particularly preferred embodiments of the composition according to the invention are described below.

The pearlizing wax can be present as first constituent in the composition according to the invention in an amount of at least 10% by weight, more preferably at least 15% by weight, even more preferably at least 18% by weight, based in each case on the composition.

The pearlizing wax can be present in the composition according to the invention in an amount of at most 40% by weight, more preferably at most 35% by weight, even more preferably at most 30% by weight, based in each case on the composition.

The pearlizing wax is preferably present in the composition according to the invention in an amount of 10% by weight to 40% by weight, more preferably 15% by weight to 35% by weight and even more preferably 18% by weight to 35% by weight, based in each case on the composition.

The non-ionic surfactant can be present as second constituent of the composition according to the invention in an amount of at least 5% by weight, more preferably at least 10% by weight, even more preferably at least 12% by weight, based in each case on the composition.

The non-ionic surfactant can be present in the composition according to the invention in an amount of at most 40% by weight, more preferably at most 35% by weight, even more preferably at most 30% by weight, based in each case on the composition.

The non-ionic surfactant is preferably present in the composition according to the invention in an amount of 5% by weight to 40% by weight, more preferably 10% by weight to 35% by weight and even more preferably 12% by weight to 30% by weight, based in each case on the composition.

In the composition according to the invention
the ratio by weight of isosorbide dipalmitate to isosorbide distearate is preferably from 45:55 to 1:99 and/or
the ratio by weight of isosorbide monopalmitate to isosorbide monostearate is preferably from 45:55 to 1:99 and/or the ratio by weight of palmitic acid to stearic acid is preferably from 45:55 to 1:99.

In a first particularly preferred embodiment, the composition according to the invention therefore comprises
at least one pearlizing wax as described above in an amount of 10 to 40% by weight; and
at least one non-ionic surfactant in an amount of 5 to 40% by weight,
where the amounts are based in each case on the composition.

In a second particularly preferred embodiment, the composition according to the invention comprises:
at least one pearlizing wax as described above in an amount of 15 to 35% by weight; and
at least one non-ionic surfactant in an amount of 10 to 35% by weight,
where the amounts are based in each case on the composition.

In a third preferred embodiment, the composition according to the invention comprises:
at least one pearlizing wax as described above in an amount of 18 to 30% by weight; and
at least one non-ionic surfactant in an amount of 12 to 30% by weight,
where the amounts are based in each case on the composition.

In the first to third embodiments described above, the compositions according to the invention are particularly characterized in that the pearlizing wax comprises a mixture of isosorbide distearate, isosorbide dipalmitate and isosorbide palmitate stearate as isosorbide diester, a mixture of isosorbide monostearate and isosorbide monopalmitate as isosorbide monoester and a mixture of stearic acid and palmitic acid as fatty acid and the at least one non-ionic surfactant comprises an alkyl polyglycoside.

In the first to third embodiments described above, the compositions according to the invention are also particularly characterized in that the isosorbide diester is present in the composition according to the invention in an amount of at least 70% by weight, based on the pearlizing wax.

In the first to third embodiments described above, the compositions according to the invention are also particularly characterized in that,
the pearlizing wax comprises a mixture of isosorbide distearate, isosorbide dipalmitate and isosorbide palmitate stearate as isosorbide diester, a mixture of isosorbide monostearate and isosorbide monopalmitate as isosorbide monoester and a mixture of stearic acid and palmitic acid as fatty acid;
the at least one non-ionic surfactant comprises an alkyl polyglycoside;
the isosorbide diester is present in the composition according to the invention in an amount of 75% by weight to 95% by weight, more preferably 80% by weight to 90% by weight and more preferably still 82% by weight to 88% by weight, based in each case on the pearlizing wax as first constituent of the composition according to the invention.

In the first to third embodiments described above, the compositions according to the invention are also particularly characterized in that,
the pearlizing wax comprises a mixture of isosorbide distearate, isosorbide dipalmitate and isosorbide palmitate stearate as isosorbide diester, a mixture of isosorbide monostearate and isosorbide monopalmitate as isosorbide monoester and a mixture of stearic acid and palmitic acid as fatty acid;

the at least one non-ionic surfactant comprises an alkyl polyglycoside;

the ratio of isosorbide dipalmitate to isosorbide distearate is from 45:55 to 1:99, more preferably from 40:60 to 1:99, more preferably still from 30:70 to 1:99, more preferably still from 30:70 to 2:98;

the ratio of isosorbide monopalmitate to isosorbide monostearate is from 45:55 to 1:99, more preferably from 40:60 to 1:99, more preferably still from 30:70 to 1:99, more preferably still from 30:70 to 2:98; and the ratio of palmitic acid to stearic acid is from 45:55 to 1:99, more preferably from 40:60 to 1:99, more preferably still from 30:70 to 1:99, more preferably still from 30:70 to 2:98.

In the first to third embodiments described above, the compositions according to the invention are furthermore particularly characterized in that the fatty acid content in the composition is at most 10% by weight, even more preferably at most 5% by weight, based in each case on the composition according to the invention.

In a very particularly preferred embodiment of the present invention, the composition according to the invention comprises 10 to 40% by weight of a pearlizing wax as first constituent, comprising
  isosorbide distearate, isosorbide dipalmitate and isosorbide palmitate stearate in an amount of 75 to 95% by weight, based on the pearlizing wax, with a ratio of isosorbide dipalmitate to isosorbide distearate from 30:70 to 2:98;
  isosorbide monostearate and isosorbide monopalmitate in an amount of 0.01 to 20% by weight, based on the pearlizing wax, with a ratio of isosorbide monopalmitate to isosorbide monostearate from 30:70 to 2:98;
  stearic acid and palmitic acid in an amount of 1 to 30% by weight, based on the pearlizing wax, with a ratio of palmitic acid to stearic acid from 30:70 to 2:98; and
5 to 40% by weight of a polyalkyl glycoside as non-ionic surfactant as second constituent,
wherein the amounts of first and second constituent are based on the composition.

In a further very particularly preferred embodiment of the present invention, the composition according to the invention comprises
15 to 35% by weight of a pearlizing wax as first constituent, comprising
  isosorbide distearate, isosorbide dipalmitate and isosorbide palmitate stearate in an amount of 80 to 90% by weight, based on the pearlizing wax, with a ratio of isosorbide dipalmitate to isosorbide distearate from 30:70 to 2:98;
  isosorbide monostearate and isosorbide monopalmitate in an amount of 0.5 to 15% by weight, based on the pearlizing wax, with a ratio of isosorbide monopalmitate to isosorbide monostearate from 30:70 to 2:98;
  stearic acid and palmitic acid in an amount of 3 to 25% by weight, based on the pearlizing wax, with a ratio of palmitic acid to stearic acid from 30:70 to 2:98; and
10 to 35% by weight of a polyalkyl glycoside as non-ionic surfactant as second constituent,
wherein the amounts of first and second constituent are based on the composition.

In a very particularly preferred embodiment of the present invention, the composition according to the invention comprises:
18 to 30% by weight of a pearlizing wax as first constituent, comprising
  isosorbide distearate, isosorbide dipalmitate and isosorbide palmitate stearate in an amount of 82 to 88% by weight, based on the pearlizing wax, with a ratio of isosorbide dipalmitate to isosorbide distearate from 30:70 to 2:98;
  isosorbide monostearate and isosorbide monopalmitate in an amount of 1 to 10% by weight, based on the pearlizing wax, with a ratio of isosorbide monopalmitate to isosorbide monostearate from 30:70 to 2:98;
  stearic acid and palmitic acid in an amount of 5 to 20% by weight, based on the pearlizing wax, with a ratio of palmitic acid to stearic acid from 30:70 to 2:98; and
12 to 30% by weight of a polyalkyl glycoside as non-ionic surfactant as second constituent,
wherein the amounts of first and second constituent are based on the composition.

In an additional preferred independent embodiment of the present invention, the composition according to the invention is characterized in that the ratio by weight of diesters of the isosorbide to monoesters of the isosorbide in the composition is at least 4:1, more preferably at least 6:1, more preferably still at least 8:1, more preferably still at least 10:1.

The composition according to the invention is used in particular as a pearlescent concentrate in which it is formulated with polyols and water.

The polyols can be present in these pearlescent concentrates in amounts of up to 40% by weight, in particular 0.1 to 30% by weight, more preferably 0.2 to 20% by weight, based in each case on the pearlescent concentrate.

Polyols which are suitable here preferably have 2 to 15 carbon atoms and at least two hydroxyl groups. Particularly suitable polyols are glycerol and/or sorbitol.

Furthermore, water is also present to make up to 100% by weight.

In particular, a pearlescent concentrate according to the invention results comprising
(a) 10 to 40% by weight pearlizing wax;
(b) 5 to 40% by weight non-ionic surfactant;
(c) 0 to 40% by weight polyol; and
(D) up to 100% by weight water.

In the context of the present invention, a pearlescent concentrate is understood to mean a mixture of the composition according to the invention in water with polyol optionally additionally used. This pearlescent concentrate may be introduced into aqueous surfactant-containing formulations, which are then commercially available formulations which serve for the final application as cosmetic composition.

The pearlescent concentrate optionally formulated with polyol and water may be prepared according to the invention by
  heating the pearlizing wax as first constituent and the non-ionic surfactant as second constituent and also optionally the polyols and water up to 100% by weight with stirring at temperatures which are 5 to 20° C. above the melting point of the pearlizing wax,
  stirring the mixture at these temperatures and
  subsequently cooling the mixture to around room temperature (20 to 23° C.) with constant stirring.

It is also possible to prepare the pearlescent concentrate by
  stirring the pearlescent concentrate into an aqueous paste of the non-ionic surfactant and heating to temperatures which are 5 to 20° C. above the melting point of the pearlizing wax,
  stirring the mixture at these temperatures and subsequently adjusting to the desired concentration with further water and optionally polyols.

In general, a stirring time of the mixture of about 15 to 60 minutes is recommended before preferably cooling the mixture at a cooling rate of about 10 to 30° C., preferably 15 to 25° C. per hour.

The pearlescent concentrates according to the invention are free-flowing mixtures which can be easily stirred into aqueous surfactant-containing preparations and produce therein a brilliant luster with a high degree of whiteness.

The isosorbide esters used in the composition according to the invention can be synthesized by esterification processes known per se. WO 01/83488 A discloses, by way of example, a suitable method by which mono- or diesters of the isosorbide or mixtures of mono- and diesters of the isosorbide can be obtained.

The present invention accordingly also relates to a method for preparing a composition according to the invention which is characterized by an esterification product being obtained by the process stage of the esterification of isosorbide with at least one saturated $C_{12}$-$C_{24}$ fatty acid.

The method according to the invention can in this connection be carried out in the presence of an esterification catalyst, tin oxalate representing a suitable catalyst.

If, in the context of the present invention, an esterification catalyst is used, the esterification catalyst used is generally deactivated after the esterification reaction; in particular, the esterification catalyst used is hydrolyzed.

Subsequent to the esterification reaction and the deactivation of the catalyst which is optionally to be carried out, the resulting reaction product is usually purified, for example by filtration or distillation under vacuum.

The esterification itself is generally carried out at a temperature of 160 to 230° C., more preferably 170 to 220° C. and more preferably still 180 to 220° C.

It should be taken into consideration, in the preparation of the mono- and diesters of the isosorbide, that depending on the excess of the isosorbide used or of the $C_{12}$-$C_{24}$ fatty acid, a variable ratio of mono- and diester is produced since the two hydroxyl groups, due to their exo- or endo-arrangement, have different reactivities.

In the method according to the invention, an excess of $C_{12}$-$C_{24}$ fatty acid to isosorbide of at least 2.05 equivalents of fatty acid, based on 1 equivalent of isosorbide, is generally used. Particular preference is given to an excess of fatty acid to isosorbide of 2.05 to 2.5 equivalents, more preferably 2.1 to 2.4 equivalents and more preferably still 2.1 to 2.2 equivalents, based in each case on 1 equivalent of isosorbide.

The method according to the invention is generally carried out, with this excess of $C_{12}$-$C_{24}$ fatty acid, for long enough for the amounts of constituents (A), (B) and (C) defined according to the invention in the claimed composition to be obtained. This is ascertainable by a person skilled in the art with the usual measures, for example by means of GC monitoring and acid number determination. Accordingly, the composition according to the invention is preferably prepared in a one-pot reaction, in which the isosorbide diester and isosorbide monoester are formed simultaneously starting from isosorbide and one or more $C_{12}$-$C_{24}$ fatty acids. Through the use of an excess of fatty acid, a residue of this likewise remains in the composition according to the invention. Admittedly, the composition according to the invention can also be prepared through the mixing of the individual constituents.

Use in Cosmetic Compositions

The composition according to the invention can preferably be used as pearlizing agent in cosmetic compositions, in particular surface-active cosmetic compositions. The cosmetic compositions, in particular surface-active cosmetic compositions, are generally liquid cosmetic compositions.

"Cosmetic compositions" are to be understood here as all compositions known to a person skilled in the art which are exclusively or primarily intended to be applied externally to the human body or inside the oral cavity for the cleaning, caring, protection, and maintaining of a good condition, perfuming, changing the appearance or for influencing body odor.

The cosmetic compositions according to the invention can in particular be formulations for body care, for example a body milk, creams, lotions, sprayable emulsions, products for eliminating body odor, and the like. The hydrocarbons can also be used in surfactant-containing formulations, such as, for example, foam baths, shower gels, shampoos and conditioners. According to the end application, the cosmetic formulations comprise a series of further auxiliaries and additives, such as, for example, surfactants, further oil bodies, emulsifiers, pearlizing waxes, bodying agents, thickeners, superfatting agents, stabilizers, polymers, fats, waxes, lecithins, phospholipids, biogenic active ingredients, UV sunscreen factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, and the like, which are listed below by way of example.

Anionic, cationic and/or amphoteric or zwitterionic surfactants may be present as further surface-active substances (surfactants). At least one anionic surfactant is preferably present in surfactant-containing cosmetic formulations, such as, for example, shower gels, foam baths, shampoos, etc. The proportion of the surfactants here is generally about 1 to 30%, preferably 5 to 25% and especially 10 to 20% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based plant products) and alkyl (ether) phosphates. If the anionic surfactants comprise polyglycol ether chains, these may exhibit a conventional homolog distribution but preferably a narrow homolog distribution.

Typical examples of cationic surfactants are quaternary ammonium compounds, such as, for example, dimethyldistearylammonium chloride, and esterquats, in particular quaternized fatty acid trialkanolamine ester salts. Typical examples of amphoteric or zwitterionic surfactants are alkyl betaines, alkyl amido betaines, aminopropionates, aminoglycinates, imidazolinium betaines and sulfobetaines. The surfactants mentioned are exclusively known compounds. With regard to the structure and preparation of these substances, reference may be made to relevant review works in this field. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkyl amido betaines, amphoacetals and/or protein fatty acid condensates, the latter preferably based on wheat proteins.

Body care compositions, such as creams, lotions and milks, typically comprise a number of further oil bodies and emollients, which contribute to further optimization of the sensory properties. The oil bodies are generally present in a total amount of 1 to 50% by weight, preferably 5 to 25% by weight and in particular 5 to 15% by weight. As further oil bodies come, for example, Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of linear $C_6$-$C_{22}$ fatty acids with branched alcohols, in particular 2-ethylhexanol, esters of $C_{18}$-$C_{38}$ alkylhydroxycarboxylic acids with linear or branched $C_6$-$C_{22}$ fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$ alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols.

Fats and waxes are added to the body care products as care substances, and also in order to increase the consistency of the cosmetics. Typical examples of fats are glycerides, i.e. solid vegetable or animal products which are composed essentially of mixed glycerol esters of higher fatty acids. Fatty acid partial glycerides, i.e. technical-grade mono- and/or diesters of glycerol with fatty acids having 12 to 18 carbon atoms, such as, for instance, glycerol mono/dilaurate, -palmitate or -stearate, are also possible for this purpose. Possible waxes are, inter alia, natural waxes, such as, for example, candelilla wax, carnauba wax, japan wax, esparto grass wax, cork wax, guaruma wax, rice bran wax, sugarcane wax, ouricury wax, montan wax, beeswax, shellac wax, spermaceti, lanolin (wool wax), uropygial grease, ceresin, ozokerite (earth wax), petrolatum, paraffin waxes, micro waxes; chemically modified waxes (hard waxes), such as, for example, montan ester waxes, Sasol waxes, hydrogenated jojoba waxes, and also synthetic waxes, such as, for example, polyalkylene waxes and polyethylene glycol waxes. As well as the fats, fat-like substances, such as lecithins and phospholipids, are also possible as additives. Examples of natural lecithins which may be mentioned are the cephalins, which are also referred to as phosphatidic acids and are derivatives of 1,2-diacyl-sn-glycerol-3-phosphoric acids. In contrast, phospholipids are usually understood to mean mono- and preferably diesters of phosphoric acid with glycerol (glycerol phosphates), which are generally counted among the fats. In addition, sphingosines or sphingolipids are also possible.

Suitable thickeners are, for example, Aerosil grades (hydrophilic silicas), polysaccharides, in particular xanthan gum, guar gum, agar, alginates and tyloses, carboxymethylcellulose, hydroxyethylcellulose and hydroxypropylcellulose, polyvinyl alcohol, polyvinylpyrrolidone and bentonites, such as, for example, Bentone® Gel VS-5PC (Rheox).

UV light protection factors are understood to mean, for example, organic substances (light protection screening agents) which are liquid or crystalline at room temperature and which are capable of absorbing ultraviolet rays and of again releasing the energy absorbed in the form of radiation of longer wavelength, for example heat. UV-B screening agents can be oil-soluble or water-soluble. Benzoylmethane derivatives are possible in particular as typical UV-A screening agents. The UV-A and UV-B screening agents can, of course, also be used in mixtures, e.g. combinations of the benzoylmethane derivatives, e.g. 4-tert-butyl-4'-methoxydibenzoylmethane (Parsol® 1789), and 2-ethylhexyl 2-cyano-3,3-phenylcinnamate (octocrylene), and also esters of cinnamic acid, preferably 2-ethylhexyl 4-methoxycinnamate and/or propyl 4-methoxycinnamate and/or isoamyl 4-methoxycinnamate. Such combinations are frequently combined with water-soluble screening agents, such as, for example, 2-phenylbenzimidazole-5-sulfonic acid and the alkali metal, alkaline earth metal, ammonium, alkylammonium, alkanolammonium and glucammonium salts thereof.

Apart from the soluble substances mentioned, insoluble light protection pigments, namely finely dispersed metal oxides, are also possible. Examples of suitable metal oxides are in particular zinc oxide and titanium dioxide. Apart from the two abovementioned groups of primary light protection substances, it is also possible to use secondary light protection agents of the antioxidant type, which interrupt the photochemical reaction chain which is triggered when UV radiation penetrates into the skin.

Biogenic active ingredients are understood to mean, for example, tocopherol, tocopherol acetate, tocopherol palmitate, ascorbic acid, (deoxy)ribonucleic acid and the fragmentation products thereof, β-glucans, retinol, bisabolol, allantoin, phytantriol, panthenol, AHA acids, amino acids, ceramides, pseudoceramides, essential oils, plant extracts, such as, for example, Prunus extract, bambara nut extract and vitamin complexes.

Deodorizing active ingredients counteract body odors, conceal or remove them. Body odors arise through the action of skin bacteria on apocrine perspiration, which forms unpleasant-smelling degradation products. Correspondingly suitable as deodorizing active ingredients are, inter alia, germination inhibitors, enzyme inhibitors, odor absorbers or odor masking agents.

Possible insect repellents are, for example, N,N-diethyl-m-toluamide, 1,2-pentanediol or ethyl 3-(N-(n-butyl)-N-acetylamino)propionate, which is sold under the description Insect Repellent® 3535 by Merck KGaA, and also butyl acetylaminopropionates.

Dihydroxyacetone is suitable as self-tanning agent. Possible tyrosine inhibitors, which prevent the formation of melanin and are applied in depigmenting compositions, are, for example, arbutin, ferulic acid, kojic acid, coumaric acid and ascorbic acid (vitamin C).

Examples of suitable preservatives are phenoxyethanol, formaldehyde solution, parabens, pentanediol or sorbic acid, and also the silver complexes known under the description Surfacine®, and the additional substance classes listed in Annex 6, parts A and B, of the Cosmetics Directive.

Mention may be made, as perfume oils, of mixtures of natural and synthetic odorants. Natural odorants are extracts of flowers, stems and leaves, fruit, fruit shells, roots, wood, herbs and grasses, needles and branches, resins and balsams. Additionally possible are animal raw materials, such as, for example, civet and castoreum, and also synthetic odorant compounds of the ester, ether, aldehyde, ketone, alcohol and hydrocarbon type.

The cosmetic compositions comprise the compositions claimed according to the invention as pearlizing agent. Admittedly, the cosmetic compositions can also comprise additional pearlizing agents. In this sense, the following, for example, are possible as pearlizing waxes, in particular for use in surface-active formulations: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted, carboxylic acids with fatty alcohols having 6 to 22 carbon atoms, especially long-chain esters of tartaric acid; fatty substances, such as, for example, fatty alcohols, fatty ketones, fatty aldehydes, fatty ethers and fatty carbonates, which have in total at least 24 carbon atoms, especially laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols (without the sorbitan derivatives) having 2 to 15 carbon atoms and 2 to 10 hydroxyl groups, and mixtures thereof.

Use may be made, as superfatting agents, of substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers.

Use may be made, as stabilizers, of metal salts of fatty acids, such as, e.g., magnesium stearate or ricinoleate, aluminum stearate or ricinoleate and/or zinc stearate or ricinoleate.

Use may furthermore be made, in order to improve the flow behavior, of hydrotropes, such as, for example, ethanol, isopropyl alcohol or polyols. Polyols which are suitable here preferably have 2 to 15 carbon atoms and at least two hydroxyl groups. The polyols may comprise still other functional groups, in particular amino groups, or be modified with nitrogen.

In particular, those cosmetic compositions are preferred which exhibit an aqueous phase and an oily phase simultaneously and exist, e.g., in the form of an emulsion (both water-in-oil and oil-in-water) and which comprise, as a constituent, one or more isosorbide derivatives according to the above definition. In this connection, the isosorbide derivatives can be used as oily phase or emollient, or as constituent of the oily phase. However, as is still explained subsequently, they can, depending on their structure, also impart certain functional properties.

The composition according to the invention is used in the cosmetic compositions as pearlizing agent, preferably in an amount of at least 0.1% by weight, based on the cosmetic composition.

The composition according to the invention is preferably used in the cosmetic composition in an amount of 0.1 to 12% by weight, more preferably 0.5 to 6% by weight and more preferably still 0.75 to 3.5% by weight, each time based on the cosmetic composition, in particular surface-active cosmetic composition.

WORKING EXAMPLES

The investigations described below were carried out on the properties of the isosorbide derivatives. Insofar as ingredients are mentioned, the INCI nomenclature has been used.

The pearlescence was assessed visually by comparison of the pearlescent concentrate of the inventive formulations 1, 2 and 3 with a standard pearlizing agent (EGDS=Cutina® AGS; comparative formulations 1 to 3) and evaluated on a scale of 0 to 2 (0=no pearlescence, 1=pearlescence comparable with standard, 2=pearlescence better than standard).

Composition of Isosorbide Diester, Isosorbide Monoester and Fatty Acid with Corresponding Carbon Chain Distribution Between $C_{16}$ and $C_{18}$:

| Carbon chain distribution | | GC wt % | | |
|---|---|---|---|---|
| $C_{16}$ and $C_{18}$ | | Mono- | Di- | Fatty |
| % $C_{16}$ | % $C_{18}$ | ester | ester | acid |
| Sample 1 | 2 | 98 | 6 | 86 | 8 |
| Sample 2 | 30 | 70 | 3 | 89 | 8 |
| Sample 3 | 45 | 55 | 4 | 83 | 13 |

Pearlescent Concentrate in which the Abovementioned Mixtures of Isosorbide Diester, Isosorbide Monoester and Fatty Acid (as Constituent I) were Used:

| | Formulations | | | | | |
|---|---|---|---|---|---|---|
| | Inventive formulation 1 | Comparison to inventive formulation 1 | Inventive formulation 2 | Comparison to inventive formulation 2 | Inventive formulation 3 | Comparison to inventive formulation 3 |
| | | | Amount (% by wt.) | | | |
| Inventive test substance isosorbide diester, | 21.4 | | 20 | | 19.5 | |

-continued

| | Inventive formulation 1 | Comparison to inventive formulation 1 | Inventive formulation 2 | Comparison to inventive formulation 2 | Inventive formulation 3 | Comparison to inventive formulation 3 |
|---|---|---|---|---|---|---|
| | | | Amount (% by wt.) | | | |
| isosorbide monoester, fatty acid) | | | | | | |
| Cutina ® AGS (ethylene glycol distearate) (comparative) | | 21.4 | | 20 | | 19.5 |
| Comperlan ® 100 (INCI: Cocamide MEA) | | | | | | |
| Monomuls ® 90-O 18 (INCI: Glyceryl Oleate) | 1.9 | 1.9 | | | | |
| Cutina ® GMS-V (INCI: Glyceryl Stearate) | 1.5 | 1.5 | | | | |
| Plantacare ® 1200 (INCI: Lauryl Glucoside, 51.5%) | 15 | 15 | 37 | 37 | 36.5 | 36.5 |
| Glucopon ® 215 CSUP (INCI: Decyl glucoside, 64%) | 8.7 | 8.7 | 13.8 | 13.8 | 3.1 | 3.1 |
| Texapon ® N70 (INCI: Sodium Laureth Sulfate 70%) | | | | | | |
| Glycerol (99.5%) | | | 15.6 | 15.6 | | |
| Benzoic acid | 0.5 | 0.5 | | | 0.4 | 0.4 |
| Citric acid (50%) | 2.3 | 2.3 | 9.8 | 9.8 | 3.9 | 3.9 |
| Water | to 100 | to 100 | to 100 | to 100 | to 100 | to 100 |
| pH | 4-5 | 4-5 | 4-5 | 4-5 | 4-5 | 4-5 |

The pearlescent concentrates were then introduced into aqueous hair shampoo formulations by mixing the following constituents at 25° C.:

4% by weight of the pearlescent concentrates,
15% by weight Texapon ® N 70 (coconut fatty alcohol + 2EO-sulfate-sodium salt)
3% by weight Dehyton ® PK45 (coconut fatty acid betaine, zwitter-ionic surfactant),
1.5% by weight sodium chloride and
1.5% by weight Plantacare ® 8/18 (=coconut alkyl glucoside; non-ionic surfactant) and up to 100% by weight water and preservatives.

Results of the Pearlescence Evaluation (Based in Each Case on the Corresponding Comparative Formulations):

| | Formulation 1 | Formulation 2 | Formulation 3 |
|---|---|---|---|
| Sample 1 | 2 | 2 | 2 |
| Sample 2 | 2 | 1 | 1 |
| Sample 3 | 1 | 1 | 1 |

The improvement of the pearlescence was determined in comparison with the comparative formulations specified in the table above, which comprise an amount of standard pearlizing agent (EGDS=Cutina® AGS) equivalent to the pearlizing wax according to the invention.

The invention claimed is:

1. A composition comprising:
    a pearlizing wax as a first constituent, the pearlizing wax comprising: (i) isosorbide diesters comprising isosorbide distearate, isosorbide dipalmitate, and isosorbide palmitate stearate, (ii) isosorbide monoesters comprising isosorbide monostearate and isosorbide monopalmitate, and (iii) fatty acids comprising stearic acid and palmitic acid; and
    a non-ionic surfactant as a second constituent,
    wherein the composition comprises:
        (a) 10 to 40% by weight pearlizing wax;
        (b) 5 to 40% by weight non-ionic surfactant;
        (c) 0 to 40% by weight polyol; and
        (d) up to 100% by weight water.

2. The composition as claimed in claim 1, wherein the isosorbide diesters are present in the composition in an amount of at least 70% by weight, based on the pearlizing wax.

3. The composition as claimed in claim 1, wherein a ratio by weight of isosorbide diesters to isosorbide monoesters in the composition is at least 4:1.

4. The composition as claimed in claim 1, wherein a ratio by weight of isosorbide dipalmitate to isosorbide distearate in the composition is from 45:55 to 1:99, a ratio by weight of isosorbide monopalmitate to isosorbide monostearate is from 45:55 to 1:99, and a ratio by weight of palmitic acid to stearic acid in the composition is from 45:55 to 1:99.

5. The composition as claimed in claim 1, wherein the fatty acids are present in the composition in an amount of 1 to 20% by weight, based on the pearlizing wax.

6. The composition as claimed in claim 1, wherein the non-ionic surfactant comprises at least one alkyl polyglycoside.

7. The composition as claimed in claim 1, wherein the composition comprises the pearlizing wax as the first constituent in an amount of 18 to 35% by weight, based on the composition.

8. The composition as claimed in claim 1, wherein the composition comprises the non-ionic surfactant as the second constituent in an amount of 12 to 30% by weight, based on the composition.

9. The composition as claimed in claim 1, wherein the composition comprises the polyol in an amount of 0.1 to 30% by weight, based on the composition.

10. The composition as claimed in claim 1, wherein the composition comprises:
the pearlizing wax as the first constituent in an amount of 15 to 35% by weight, based on the composition; and
the non-ionic surfactant as the second constituent in an amount of 10 to 35% by weight, based on the composition.

11. The composition as claimed in claim 10, wherein a ratio by weight of isosorbide dipalmitate to isosorbide distearate in the composition is from 45:55 to 1:99, a ratio by weight of isosorbide monopalmitate to isosorbide monostearate is from 45:55 to 1:99, and a ratio by weight of palmitic acid to stearic acid in the composition is from 45:55 to 1:99.

12. The composition as claimed in claim 11, wherein:
the isosorbide diesters are present in the composition in an amount of at least 70% by weight, based on the pearlizing wax;
a ratio by weight of isosorbide diesters to isosorbide monoesters in the composition is at least 4:1; and
the fatty acids are present in the composition in an amount of 1 to 20% by weight, based on the pearlizing wax.

13. The composition as claimed in claim 12, wherein the composition comprises the polyol in an amount of 0.1 to 30% by weight, based on the composition.

14. A method for preparing a composition as claimed in claim 1, the method comprising:

(a) esterifying isosorbide with fatty acids comprising stearic acid and palmitic acid to obtain an esterification product pearlizing wax as the first constituent, the pearlizing wax comprising: (i) isosorbide diesters comprising isosorbide distearate, isosorbide dipalmitate, and isosorbide palmitate stearate, (ii) isosorbide monoesters comprising isosorbide monostearate and isosorbide monopalmitate, and (iii) fatty acids comprising stearic acid and palmitic acid, and (b) mixing the esterification product pearlizinq wax from step (a) with the second constituent comprising the non-ionic surfactant to form the composition, wherein the composition comprises:
(i) 10 to 40% by weight pearlizinq wax;
(ii) 5 to 40% by weight non-ionic surfactant;
(iii) 0 to 40% by weight polyol; and
(iv) up to 100% by weight water.

15. A method for preparing an aqueous surface-active preparation with pearlescent effect, the method comprising:
adding the composition of claim 1 to an aqueous surfactant-containing composition.

16. The method of claim 15, wherein the composition of claim 1 is added to the aqueous surfactant-containing composition in an amount of 0.2 to 10% by weight relative to the aqueous surface-active preparation with pearlescent effect.

* * * * *